United States Patent [19]

Birchmeier et al.

[11] Patent Number: 4,591,792

[45] Date of Patent: May 27, 1986

[54] METHOD AND APPARATUS FOR MEASURING THE POLARIZED POTENTIAL OF A BURIED OR SUBMERGED STRUCTURE PROTECTED BY IMPRESSED CURRENT

[75] Inventors: John R. Birchmeier, Columbus; George T. Ruck, Worthington; Neil G. Thompson, Dublin; Thomas J. Barlo, Columbus, all of Ohio

[73] Assignee: Gas Research Institute, Chicago, Ill.

[21] Appl. No.: 578,069

[22] Filed: Feb. 8, 1984

[51] Int. Cl.[4] ............................................. G01N 27/00
[52] U.S. Cl. .................................... 324/425; 324/71.1
[58] Field of Search ................. 324/71.1, 65 CR, 425; 307/95; 204/196, 404, 148, 1 T

[56] References Cited

U.S. PATENT DOCUMENTS 2,803,797 9/1957 Crowles ............................... 324/425
3,821,642 6/1974 Seymour ......................... 324/65 CR Primary Examiner—Reinhard J. Eisenzopf
Assistant Examiner—G. Peterkin
Attorney, Agent, or Firm—Robert B. Watkins

[57] ABSTRACT

The polarized potential at the boundary between a submerged pipe and a medium is measured unaffected by the presence of a distributed IR drop in the medium due to an impressed current from a corrosion protection system. The voltage between the pipe and a reference electrode in the medium is measured when the protection system current is zero. This is accomplished with a sample-and-hold circuit controlled by a trigger signal derived from the input signal and having a variable phase for controlling the phase angle at which the sample is taken.

11 Claims, 7 Drawing Figures

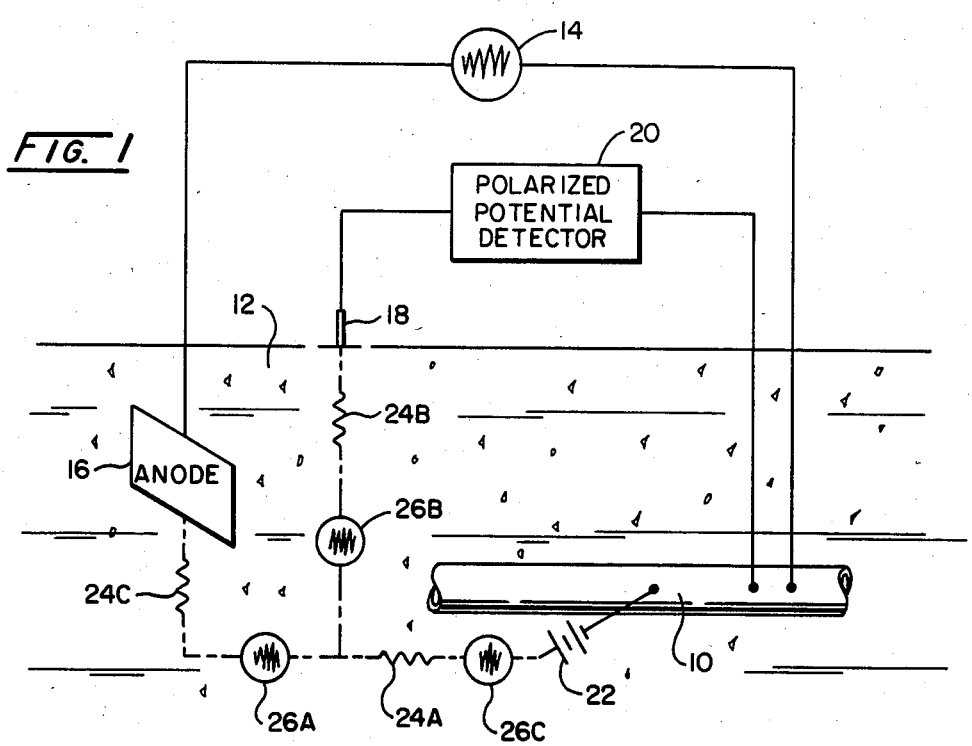

METHOD AND APPARATUS FOR MEASURING THE POLARIZED POTENTIAL OF A BURIED OR SUBMERGED STRUCTURE PROTECTED BY IMPRESSED CURRENT

TECHNICAL FIELD OF THE INVENTION

This invention relates to systems for protecting submerged structures, such as pipelines, from corrosion by applying a compensating electrical current and more particularly relates to a method and apparatus for measuring the polarized potential which is generated by the electrochemical reactions existing at the boundary between the submerged structure and its surrounding medium with the measurement being uneffected by the presence of the impressed current from the protection system.

BACKGROUND OF THE INVENTION

Submerged structures such as buried steel pipelines corrode as a result of the natural electrochemical activity at their surface. The electrochemical activity consists of an oxidation reaction, which is the corrosion process, and a reduction reaction of equal rate. The rates of these reactions are controlled by the electrochemical potential established at the submerged structure surrounding medium interface.

Protection systems to retard or prevent the corrosion reaction have been devised and are sometimes legally required. One type of protection system applies a periodic, full-wave or half-wave, rectified AC voltage between the submerged structure and a counter electrode, which is also submerged in the medium. This voltage creates a cathodic current polarizing the structure to more negative values and reducing the electron flow arising from the natural corrosion reaction distributed along the surface of the pipe or other submerged structure.

In order to determine the voltage which should be applied by the protection system between the submerged structure and the counter electrode, or in order to determine the level of protection given by an existing protection system, it is desirable to accurately measure the polarized potential which exists at the boundary region between the submerged structure and the surrounding medium. If the polarized potential generated by the protection system is insufficient, the buried structure will continue to corrode and if the polarized potential is excessive, then unnecessary and costly electrical energy will be consumed without providing proportionate protection to the submerged structure.

Conventionally the polarized potential is measured by measuring the average or DC voltage which exists between the submerged structure and a reference electrode inserted in the surrounding medium. However, such a measurement is subject to significant error because the current from the protection system causes a distributed IR drop in the surrounding medium. Additionally, other external sources also can cause errors by introducing stray currents. Therefore, the resultant voltage measured between the submerged structure and the reference electrode represents the algebraic sum of polarized potential components and the IR drop component from the protection system and all external sources.

It is therefore a principal object of the present invention to eliminate the IR drop component and the effects from external sources from the measured voltage in order to obtain a more accurate measurement of the polarized cell potential.

The conventional measuring techniques are also subject to inaccuracies due to interference from 60 Hz signals and harmonics thereof, usually from a power distribution system and from high frequency and random noise signals.

Accordingly it is another object of the invention to provide a measuring system which is insensitive to some of these interference sources and can signal the presence of others.

BRIEF DISCLOSURE OF THE INVENTION

The invention is a method and apparatus for measuring the polarized potential, which is generated at the boundary between a submerged structure and its surrounding medium, and is measured in spite of the presence of an impressed current from a protection system which applies a periodic, rectified voltage between the submerged structure and a counter electrode also submerged in the medium.

The method comprises measuring the electrochemical potential difference between the submerged structure and a stable reference electrode which is inserted in the medium. The potential is measured in a time interval when the cathode current of the protection system is zero. This is preferably accomplished by sampling the periodic signal, which appears between the reference electrode and the submerged structure, at a plurality of selected phase angles along repetitive cycles of the periodic signal and selecting the minimum sample amplitude.

The apparatus comprises a sample-and-hold circuit having its inputs connected between the reference electrode and the submerged structure to receive an input signal. Its sample output terminals are connected to an averaging means for averaging the samples. A trigger signal generator having an adjustable phase shift to accomplish a time delay is connected to the sample-and-hold circuit for selectively varying the phase of its output pulses relative to the input signal and thereby varying the positions at which the input signal is sampled. Preferably the trigger signal is derived from the input signal itself so that its phase will be easily and accurately controlled relative to the input signal.

The invention eliminates measurement of the distributed IR drop in the surrounding medium because the input potential is measured when current is not flowing. With a 60 Hz half-wave or full-wave rectified protection system, the samples are taken at a 120 Hz rate. The measurements are insensitive to 60 Hz interference whether in phase or out-of-phase with the protective system signal because the error in alternate samples will be equal and opposite and therefore will cancel each other. Averaging of the output causes the measurements to be insensitive to high frequency interference and random noise.

An alarm circuit may be used which detects and signals the presence of harmonics of 60 Hz which are out-of-phase with the protection signal. The alarm system comprises a reference generator which generates a reference signal which is phase coherent with the input protective system signal and at a frequency which is an integral multiple of the input signal. A phase comparator has one input connected to the output of the reference generator and the other input connected to a bandpass filter centered at the harmonic being sought. An alarm is connected at the output of the phase comparator and is actuated upon detection of a phase difference between the detected protection system signal and a harmonic.

BRIEF DESCRIPTION OF THE DRAWINGS

FIG. 1 is a diagrammatic illustration of a buried pipe, a protection system for the pipe and a polarized potential detector embodying the present invention.

FIG. 2 is a block diagram illustrating the fundamental polarized potential detector circuitry of the present invention and its connection to the submerged structure.

Figure 3:
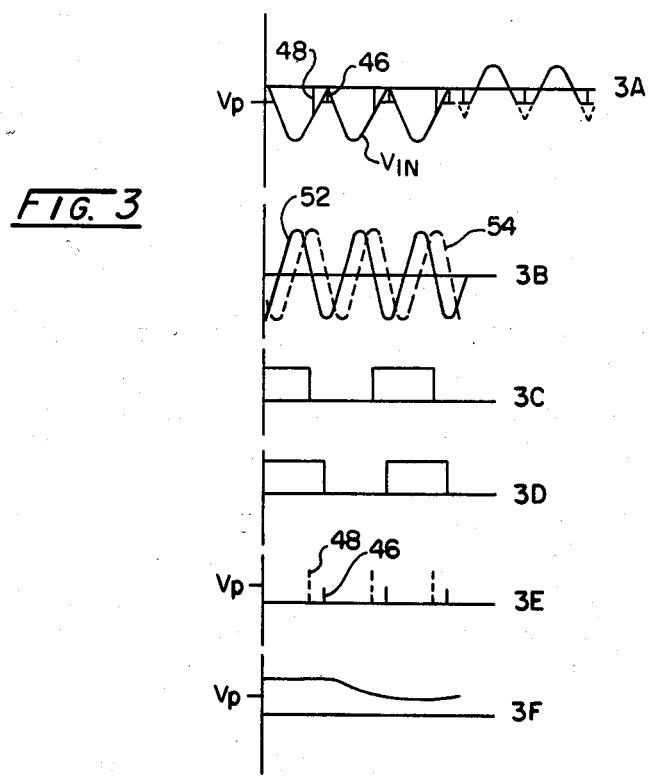
FIGS. 3A through 3F are a plurality of oscillograms illustrating the operation of the preferred embodiment of the invention.

In describing the preferred embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose. For example, the word connected or terms similar thereto are often used. They are not limited to direct connection but include connection through other circuit elements where such connection is recognized as being equivalent by those skilled in the art.

DETAILED DESCRIPTION

FIG. 1 illustrates the interconnection of a submerged structure 10, such as a pipe, in a surrounding medium 12, such as soil, and connected to a protection system 14. The protection system 14 generates a full-wave or half-wave rectified sine wave voltage which it applies to the pipe 10 and an electrode 16 also submerged in the medium 12. Ordinarily, a pipe is cathodically protected and therefore the pipe 10 is a cathode and the buried electrode 16 is an anode. As is well known to those skilled in the art, the pipe may be the anode and the counter electrode may be the cathode. This role reversal is described briefly in connection with FIG. 3A.

The polarized potential detector 20 of the present invention is also connected to the submerged structure 10 and is connected to a reference electrode 18 which is contacting the medium 12. Although the connections between the electrode 16, the reference electrode 18 and the submerged structure 10 are distributed throughout the surrounding medium 12, they are illustrated in FIG. 1 in phantom as discrete connections to discrete circuit elements. The electrochemical potential 22 which is actually distributed along the surface of the submerged structure 10 is connected through the inherent distributed resistances 24A, 24B and 24C of the surrounding medium to the reference electrode 18 and the electrode 16. Additionally, the sources of interference and noise are represented as noise generators 26A, 26B and 26C.

From FIG. 1 it can be seen that at the instant at which protective current is not flowing through the surrounding medium, the potential difference measured between the reference electrode 18 and the submerged structure 10 will be equal to the algebraic sum of the polarized potential 22 distributed along the boundary of the submerged structure 10, the sum of the sources 26, and the potential of the reference electrode 18. The reference electrode 18 can be one of several commonly used standard reference electrodes.

FIG. 2 illustrates in more detail the connection of the polarized potential detector of the present invention to the other components. The input voltage V into the polarized potential detector is the potential between the submerged structure 10 and the probe 18. This input voltage is illustrated in solid lines in FIG. 3A for a full-wave protection system. It approximates the waveform of the full-wave rectified compensating voltage applied by the protective system 14 except that it has periodic intervals in which the amplitude remains level. These intervals occur when current from the protective system is not flowing. The amplitude of these intervals represents the sum of the polarized potentials of the electrolytic cell formed at the boundary of the reference electrode 18 and the boundary of the submerged structure 10.

A high input impedance buffer 30 applies this input signal V into a sample-and-hold circuit 32. The buffer is simply an impedance matching or transforming device to permit the input signal to be received by a high impedance input device, with minimized distortion, and then applied to the sample-and-hold circuit 32. The buffer 30 is therefore inconsequential with respect to the theory of operation of the circuit.

The sample-and-hold circuit 32 is controlled at its control input 32 by an adjustable trigger signal generator means 33, outlined in a broken line, which determines the timing or phase at which the sample is taken and held. The adjustable trigger signal generator means 33 preferably comprises a series connected bandpass filter 34 having its pass band at 60 or 120 Hz for half-wave or full-wave rectified protective circuits respectively, an adjustable phase shift network 36, a phase-locked-loop 38 and a transition detector 40 controlled in the conventional manner by a clock 42. The purpose of the adjustable trigger signal generator means 33 is to generate a periodic trigger signal for triggering the sampling by the sample-and-hold circuit 32 at the desired phase angle of the input signal from the reference electrode 18. For controlling the phase angle at which the samples are taken, the trigger signal generator means 33 has a phase control input 44 which may, for example with manual control, be a potentiometer in the adjustable phase shift circuitry.

In the operation of the fundamental embodiment of the invention, the phase control input 44 is adjusted until minimum sample amplitudes are detected at the output 60. The amplitude of these minimum samples represents the polarized potential. Referring to the left most oscillogram of FIG. 3A, samples taken within the constant potential intervals, such as sample 46, represent the polarized potential. Samples taken outside the constant potential level, such as sample 48, are greater because they include the IR drop distributed in the surrounding medium.

Looking at the adjustable trigger signal generator means 33 in more detail, if the protective system generates a full-wave recified sine wave, the pass band of the pass band filter 34 will be centered at 120 Hz. The output of that filter is applied to the adjustable phase shift network 36, the output signal of which is illustrated in FIG. 3B. Two representative outputs of the phase shift network 36 are illustrated in FIG. 3B at two different phase angles.

The phase-locked-loop 38 is of the conventional type which is a free running, square wave oscillator operating at a considerably higher frequency than the input signal and having a divide-by-n-output stage for selecting the desired output frequency. It also has an output which compares the phase angle of the output of the phase-locked-loop and the phase angle of the output of the adjustable phase shift network to maintain the loop in phase synchronism with the output of the phase shift network 36. Thus, for a protection circuit using a full-wave recified sine wave, a 120 Hz output signal from the phase-locked-loop is fed back for comparison to the output of the adjustable phase shift network. A 60 Hz signal is fed back for a half-wave rectified sine wave protection circuit.

The output of the phase-locked-loop 38 is applied to a transition detector 40. The transition detector 40 is a circuit which provides an output pulse of short duration for initiating the sampling by the sample-and-hold circuit 32 in response to a transition of the square wave output from the phase-locked-loop. Thus, by varying the phase shift at the phase shift control input 44, the position of the samples may be varied and a minimum negative sample amplitude and therefore a minimum output 60 is selected. Alternatively to manual operation, the varying of the phase and the selection of the minimum sample amplitude can be done with conventional computer and electronic circuit techniques. If an anodic protection system is used, the highest most oscillogram of FIG. 3 is applicable and a maximum negative sample amplitude will be selected and will represent $V_p$.

By way of example, an output signal 52, illustrated in FIG. 3B, from the phase shift network 36 will cause the output of the phase-locked-loop 38 to be the square wave illustrated in FIG. 3C. This signal will cause samples, such as sample 48, to be taken at a 120 Hz rate. Similarly, the 120 Hz signal 54 illustrated in FIG. 3B at the output of the phase shift network 36 will cause the output of the phase-locked-loop 38 to be the square wave illustrated in FIG. 3D and result in samples such as sample 46 at a different phase or time position.

Although samples are preferably at the same rate as the frequency of the input signal, they could be taken at every other, every third, etc., cycle of the input signal. Thus, the sampling rate may be any integral division of the frequency of the output signal.

A low pass filter 50 is connected to the output of the sample-and-hold circuit 32 to provide an averaging means which averages the held samples appearing at the output of the sample-and-hold circuit 32. The output 60 will therefore have appearance illustrated in FIG. 3F as the position of the samples is varied from the position of sample 48 to the position of sample 46. The low pass filter 50 also eliminates the random noise and high frequency interference from the output samples.

Figure 4:
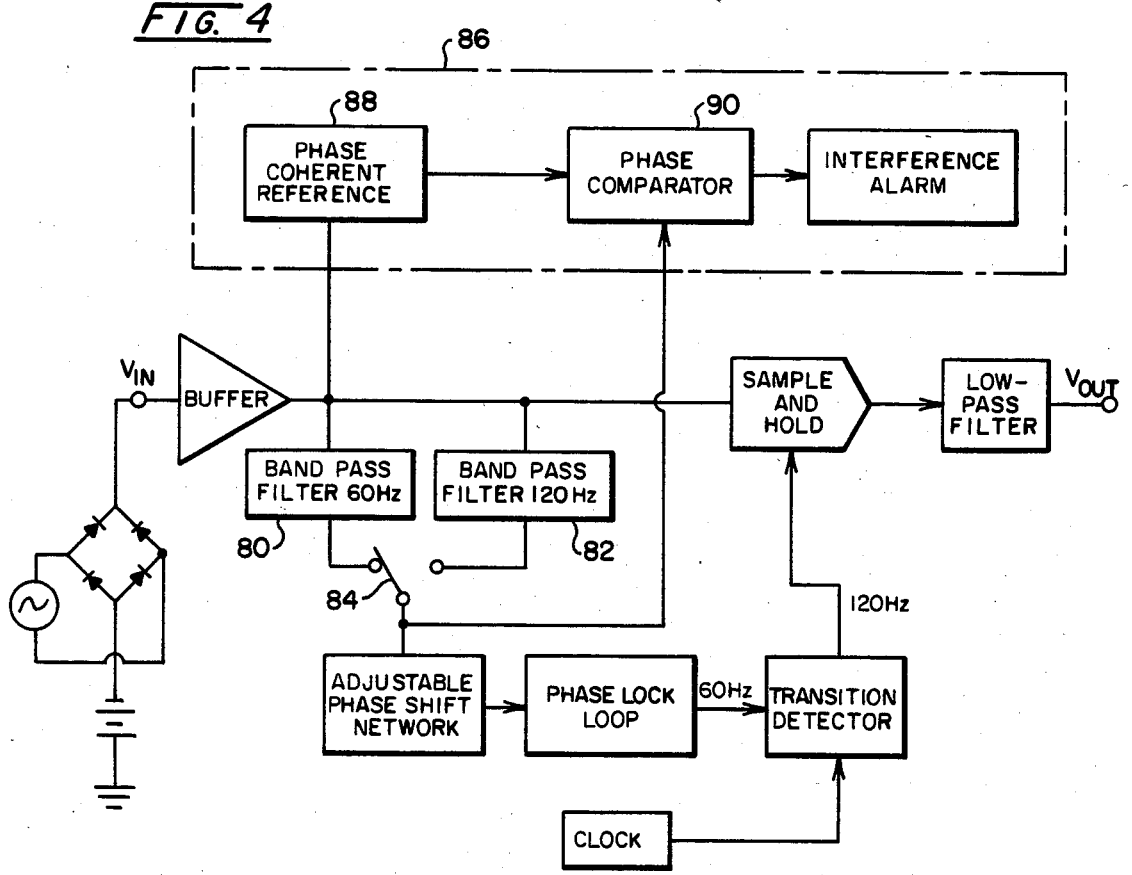
FIG. 4 is a detailed block diagram of the preferred embodiment of the invention and including the out-of-phase-harmonic alarm system of the present invention.

Referring to FIG. 4, the bandpass filter is more conveniently constructed as two separate bandpass filters 80 and 82, one having a pass band at 60 Hz and the other having a pass band at 120 Hz. The output of each bandpass filter is connected to a single pole, multiple throw switch 84 to permit convenient manual selection of either pass band which is appropriate for full-wave or half-wave rectified sine wave protection systems.

Because the system as described so far would respond to and create an error in the presence of interference from harmonics of 60 Hz which are out-of-phase with the protection circuit signal, an error alarm 86 is connected in the circuit and illustrated in FIG. 4. The error alarm includes a reference generator 88 which is connected to receive the input signal from the protection circuit. It provides a reference which is phase coherent with that input signal and at a frequency which is an integral multiple of that input signal.

A phase comparator 90 has one of its inputs connected to the output of the phase coherent reference 88 and its other input connected to the switch 84. The switch 84 must be positioned to the particular bandpass filter providing the harmonic frequency being sought. For example, if the error alarm circuit 86 is being used to determine whether an out-of-phase 120 Hz interference signal is present, the switch 84 is switched to the bandpass filter 82 so that the phase comparator 90 can continuously compare the output of the phase coherent reference 88 to any 120 Hz signal passing through the bandpass filter 82. If these signals are in phase, the alarm is not sounded. However, if the phase comparator detects that an out-of-phase 120 Hz signal is present, then the interference alarm is actuated.

Figure 5:
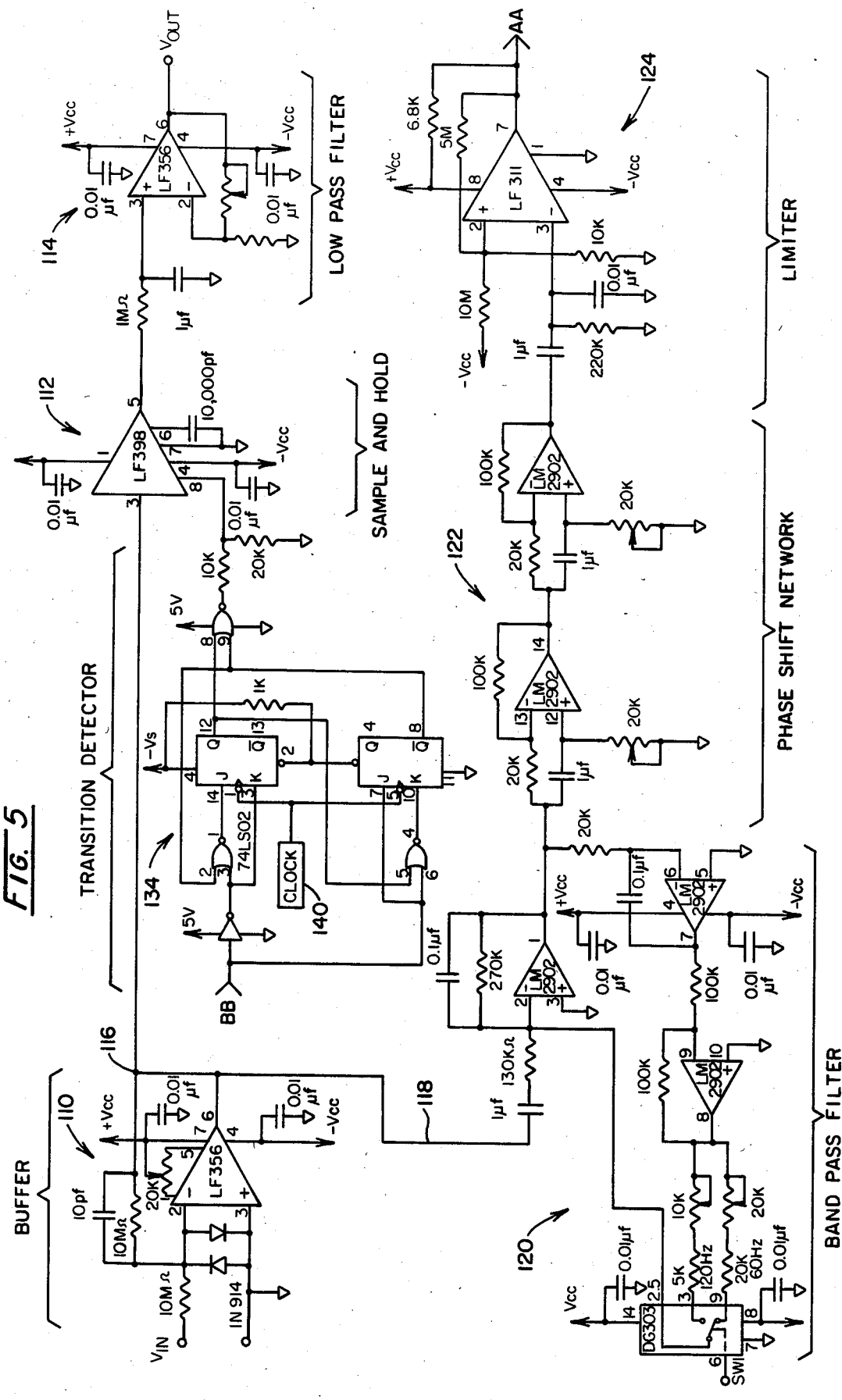
FIGS. 5, 6 and 7 together comprise a schematic diagram of the preferred embodiment of the invention.
Figure 6:
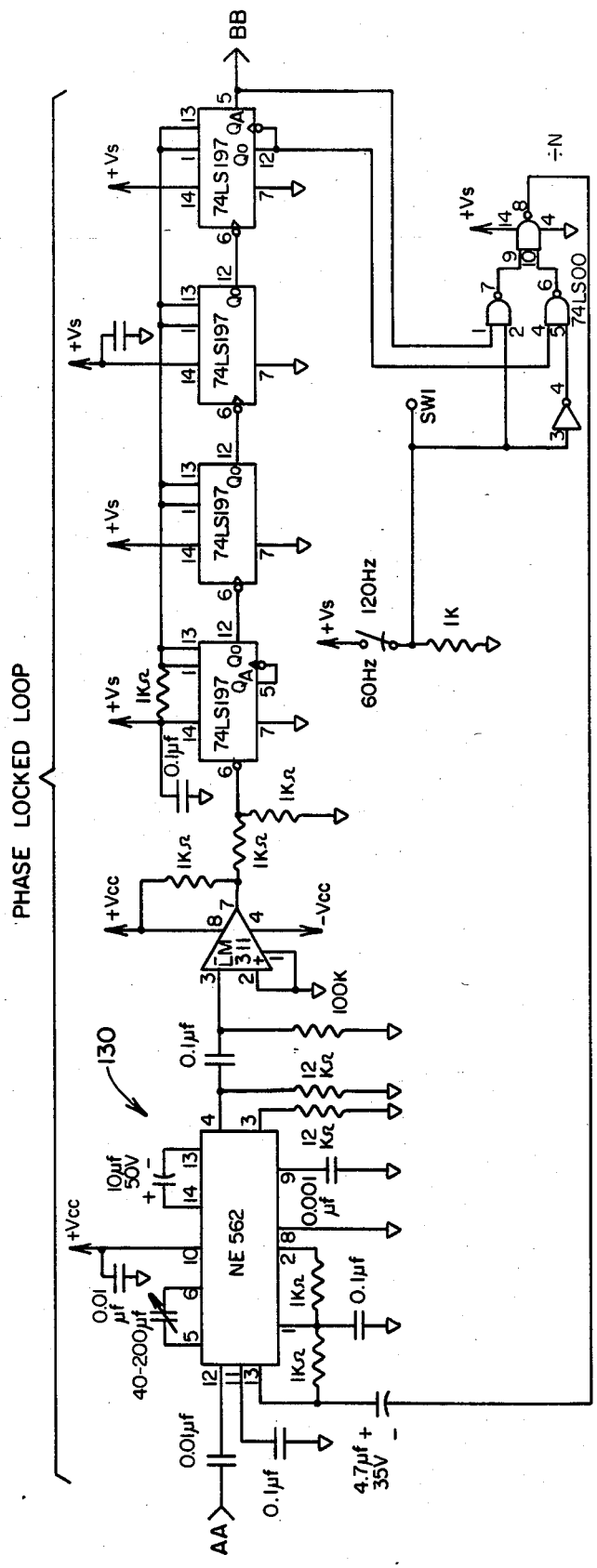
Figure 7:
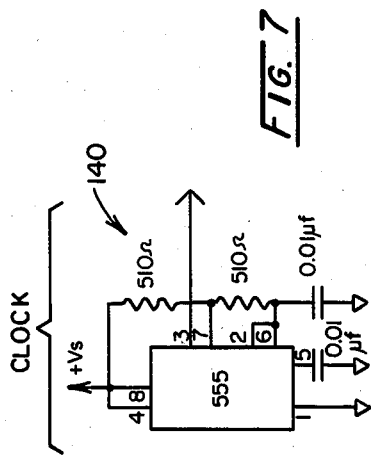

FIGS. 5, 6 and 7 are a schematic diagram of the preferred embodiment of the invention. FIG. 5 shows the buffer 110 connected to the sample-and-hold circuit 112 and the low pass filter 114. In addition, the signal from the output 116 of the buffer 110 is applied to the trigger signal generator means through conductor 118. The bandpass filter 120 is connected to the phase shift network 122 and a conventional limiter network 124. The output AA of the limiter circuit 124 is connected to the phase-locked-loop 130 illustrated in FIG. 6. The output BB from the phase-locked-loop 130 is in turn connected to the input BB to the transition detector 134 illustrated in FIG. 5. The clock circuit 140 is illustrated in detail in FIG. 7 and is shown as a block in FIG. 5.

While certain preferred embodiments of the present invention have been disclosed in detail, it is to be understood that various modifications in its structure may be adopted without departing from the spirit of the invention or the scope of the following claims.

We claim:

1. A method for measuring the polarized potential, which is generated at the boundary between a submerged structure and its surrounding medium, in the presence of a compensating cathodic or anodic current from a protection system which applies a periodic rectified voltage between said structure and a counter electrode submerged in said medium, said method comprising: measuring along the waveform of a potential difference between said submerged structure and a reference electrode inserted in said medium to find the minimum potential of that waveform and measuring said minimum potential wherein said compensating cathodic or anodic current is zero during the time interval of said minimum potential.

2. A method for measuring the polarized potential, which is generated at the boundary between a submerged structure and its surrounding medium, in the presence of a compensating cathodic or anodic current from a protection system which applies a periodic rectified voltage between said structure and a counter electrode submerged in said medium, said method comprising:

(a) detecting a periodic signal between said submerged structure and a reference electrode inserted in said medium; and (b) detecting the minimum amplitude of said periodic signal by sampling said periodic signal at a plurality of phase angles along cycles of said periodic signal and selecting the minimum sample amplitude; wherein said minimum sample amplitude represents said polarized potential.

3. A method in accordance with claim 2 wherein said minimum sample amplitude is detected by:
(a) generating a trigger signal from said detected periodic signal, said trigger signal having a selectively variable phase shift with respect to said detected periodic signal;
(b) sampling said detected periodic signal in response to said trigger signal; and
(c) varying said phase shift of the trigger signal until a minimum sample amplitude is obtained.

4. A method in accordance with claim 3 wherein the amplitude of said samples is maintained until the next sample and wherein said held samples are averaged over a period of time.

5. An apparatus for measuring the polarized potential, which is generated at the boundary between a submerged structure and its surrounding medium, in the presence of a compensating cathodic or anodic current from a protection system having a periodic, rectified voltage source connected between said structure and a counter electrode submerged in said medium, said apparatus being of the type having an input connected to said structure and to a reference electrode inserted in said medium, said apparatus comprising:
(a) a sample-and-hold means having its inputs connected to said apparatus input and having a sampling control input;
(b) an adjustable trigger signal generator means for generating a periodic trigger signal at an integral division of the frequency of said voltage source, said generator means having a phase control input for selectively varying the phase of said trigger signal with respect to the phase of said voltage source, said trigger signal generator means also having its output connected to the control input of said sample-and-hold means for initiating the sampling of the input voltage between said reference electrode and said medium in response to a trigger signal; and
(c) an averaging means connected to the output of said sample-and-hold means for outputting a signal proportional to the average amplitude of the sample levels over a recent period of time.

6. An apparatus in accordance with claim 5 wherein said trigger signal generator further comprises:
(i) circuit means having an input connected to said structure and said reference electrode for providing a first signal at its output having a frequency at an integral multiple of the signal applied to the input of said sample-and-hold circuit means; and
(ii) phase locking means for maintaining a trigger signal derived from said first signal at a selected phase angle with respect to said first signal.

7. An apparatus in accordance with claim 5 wherein said averaging circuit means comprises a low pass filter circuit.

8. An apparatus in accordance with claim 5 wherein said trigger signal generator means comprises:
(a) a bandpass filter means having its input connected to said apparatus input for passing frequencies which are integral multiples of the frequency of the signal at said apparatus input;
(b) an adjustable phase shift means having its input connected to the output of the bandpass filter means;
(c) a phase-locked-loop means connected to the output of said phase shift means for providing a rectangular wave output in phase with the output of said phase shift means; and
(d) a transition detector means connected between the output of said phase-locked-loop means and the control input of said sample-and-hold means for triggering in a sample in response to transitions of said rectangular wave output.

9. An apparatus in accordance with claim 8 further comprising an error alarm which comprises:
(a) a reference generator connected to said input of said apparatus for generating a reference signal which is phase coherent with said input voltage at a frequency which is an integral multiple thereof;
(b) a phase comparator having a pair of inputs, one input connected to the output of said reference generator and the other input connected to the output of said bandpass filter; and
(c) an alarm means connected to the output of said phase comparator for actuation in response to detection of a phase difference by said phase comparator.

10. An apparatus in accordance with claim 8 wherein said bandpass filter means comprises a plurality of bandpass filters each having a pass band centered at different integral multiples of the frequency of said input voltage, the output of each bandpass filter connected to a single pole, multi-throw switch for selection of the output of one of said bandpass filters for connecting to the input of said phase shift means.

11. An apparatus in accordance with claim 10 further comprising an error alarm which comprises:
(a) a reference generator connected to said input of said apparatus for generating a reference signal which is phase coherent with said input voltage at a frequency which is an integral multiple thereof;
(b) a phase comparator having a pair of inputs, one input connected to the output of said reference generator and the other input connected to the output of said bandpass filter; and
(c) an alarm means connected to the output of said phase comparator for actuation in response to detection of a phase difference by said phase comparator.

* * * * *